United States Patent [19]

Donnelly

[11] Patent Number: 4,477,917

[45] Date of Patent: Oct. 16, 1984

[54] DIGITAL DISDROMETER

[75] Inventor: Denis P. Donnelly, Saratoga Springs, N.Y.

[73] Assignee: Siena College, Loudonville, N.Y.

[21] Appl. No.: 247,940

[22] Filed: Mar. 26, 1981

[51] Int. Cl.³ .......................................... G01N 27/00
[52] U.S. Cl. ................................... 377/11; 73/432 PS
[58] Field of Search ........ 235/92 PC, 92 FL, 92 MT; 364/555; 73/432 PS, 432 G; 377/11, 19, 21

[56] References Cited

U.S. PATENT DOCUMENTS

| | | | |
|---|---|---|---|
| 2,825,872 | 7/1958 | Stubbs | 324/71 |
| 2,959,348 | 11/1960 | Nassenstein | 235/92 PC |
| 2,997,597 | 8/1961 | Mumma | 235/92 PC |
| 3,153,727 | 10/1964 | Nathan | 235/92 PC |
| 3,714,564 | 1/1973 | Reinnagel | 73/432 PS |
| 3,815,024 | 6/1974 | Bean et al. | 73/432 PS |
| 3,836,850 | 9/1974 | Coulter | 235/92 PC |
| 3,844,174 | 2/1974 | Chabre | 73/432 PS |
| 3,982,183 | 9/1976 | Collineau et al. | 235/92 PC |
| 4,205,384 | 5/1980 | Merz et al. | 73/432 PS |

FOREIGN PATENT DOCUMENTS 44-14646 4/1969 Japan.

OTHER PUBLICATIONS

"Digital Disdrometer" by Donnelly and Bulson, published at the Radar Meteorology Conference, Apr. 15–18, 1980.

*Primary Examiner*—Gary Chin
*Attorney, Agent, or Firm*—Heslin & Watts

[57] ABSTRACT

A plurality of thin, conductive wires are stretched across the open center of a frame through which the liquid drops to be measured will fall. Adjacent wires are maintained at a potential difference with respect to each other so that when the wires are momentarily connected by a passing conductive drop, the potential of one rises while that for the other falls. The wires are connected to circuitry which detects the change in potential in each individual wire and stores an indication of such change for later use. By counting the number of adjacent wires whose potential has changed, and knowing the dimensions of the wires and the spacing between them, it is possible to calculate drop size to accuracies dependent upon the design dimensions chosen for the device.

10 Claims, 2 Drawing Figures

DIGITAL DISDROMETER

BACKGROUND AND SUMMARY OF THE INVENTION

This invention relates to instruments and devices for measuring the size of liquid drops which are falling or otherwise moving through space.

It is often of interest to know the size of liquid drops falling or passing through a defined space. It may be of scientific interest, for example, to measure the size of raindrops under a variety of conditions, or one might wish to measure the size of drops produced by the atomization of a carburetor, the spray of an aerosol, whether it be for the spraying of a paint, lubricant or another material. Because of this interest in determining the size of liquid drops, various devices have been invented for this purpose. The particle analyzing apparatus described in U.S. Pat. No. 2,825,875 to Stubbs is an example. That invention uses a pencil-like probe 3, having an exposed spherical tip 5. The tip is in electrical contact with a sensing element 4 within probe 3 which, in turn, is connected to a source of constant potential. When an uncharged particle contacts the exposed tip 5, an electrical charge varying with the size of the particle is drawn from the sensing element 4 and momentarily reduces its potential. The negative pulse or signal thus created is detected by suitable circuitry which amplifies it and correlates particle size with pulse amplitude. The resulting data is thus the result of an indirect method of measurement. It might also be noted that the size of the sampling area in which drop sizes can be measured at any given moment is quite small. This is true even with the modified probe tips illustrated in FIGS. 4, 5 and 6 of the said patent. It can be appreciated that for laboratory purposes and for a variety of other applications, it may be desirable at times to be able to monitor a relatively larger sampling area. Furthermore, it is often desirable to obtain a direct measurement of drop size, rather than one which is dependent upon the magnitude of electrical effects related to drop size.

Devices such as those illustrated in the Stubb's patent tend to be expensive because they are relatively complicated and require the generation and use of relatively high voltages. A further disadvantage associated with such devices is that particles or drops being measured can accumulate on the sensing tip, adversely affecting their operation. Also, the distribution of drop sizes cannot be directly calculated from the output of such a device since drops of all sizes exceeding a predetermined minimum will trigger the recording circuitry. Rather, one must deduce the distribution of drop sizes by sequentially selecting drop size thresholds and noting the increase or decrease in drop indications produced for each incremental threshold change. Finally, the usefulness of such devices is over limited by the fact that only completely uncharged particles or drops can be accurately detected and measured with them.

Another approach to measuring particle or liquid drop size is illustrated by U.S. Pat. No. 4,205,384. The invention described therein employs a sensor device such as a heat image camera, which detects the physical characteristics of particulate matter in the form of measured values representing the size and/or mass and/or heat content or possibly other features thereof. While such an approach is undoubtedly suitable for applications of the type described in that patent, such apparatus does not offer the precision and the advantages associated with a direct measurement system.

The present invention centers in a novel sensing element comprised of a plurality of conductive wires held in a spaced-apart parallel array at a precisely measured distance from one another. Even numbered wires are maintained at ground potential while the odd numbered wires are maintained at a positive voltage. Whenever adjacent wires are connected by a falling electrically conductive liquid drop, the potential of the grounded wire will rise while that for the positive wire falls. Each wire is connected to circuitry which will react to the change in potential by providing an indication of such change. The circuitry enables one to count the number of adjacent wires whose potential has changed and to thereby mathematically determine the size of the drop connecting them. The accuracy of the drop size determination thus made is dependent only upon the physical limitations involved in the spacing of the wires and their diameters.

An invention of the type indicated offers the advantage of direct measurement, thereby avoiding errors characteristic of indirect measurements. Moreover, the invention is simple in design and relatively inexpensive to produce. It is capable of monitoring a relatively large sampling area which may vary in size depending upon the purpose of the sampling and the anticipated frequency of drops whose sizes are to be determined. Furthermore, it is capable of detecting and measuring either charged or uncharged drops.

DETAILED DESCRIPTION OF THE DRAWINGS

Figure 1:
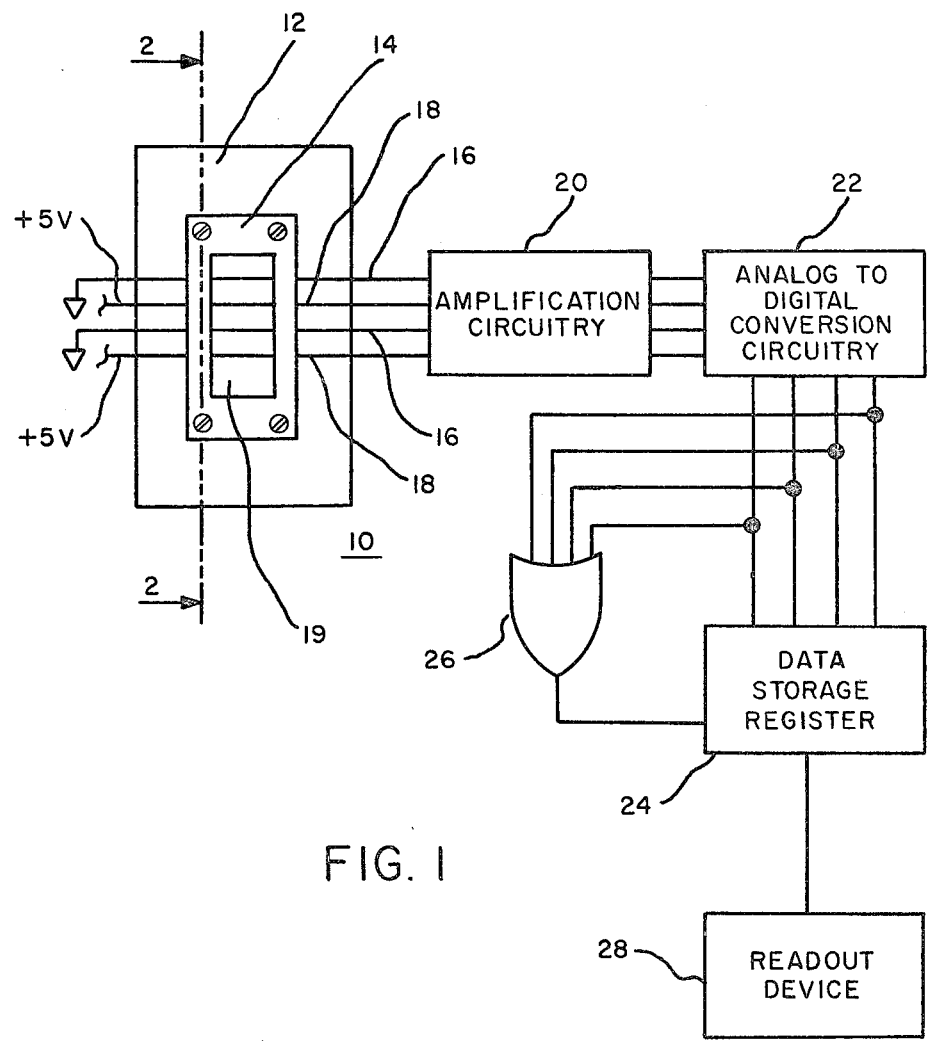
FIG. 1 is a top plan view of the detector head of this invention connected to associated circuitry shown in block form.

FIG. 1 shows a detector head 10 upon which a plurality of sensing wires 16 and 18 are stretched across a central opening 19. Wires 16 are grounded and wires 18 are maintained at a relatively small positive potential of, say, 5 volts. While, for the sake of simplicity, only four sensing wires are shown, it is to be understood that detector head 10 would normally be provided with a larger number of wires.

Figure 2:
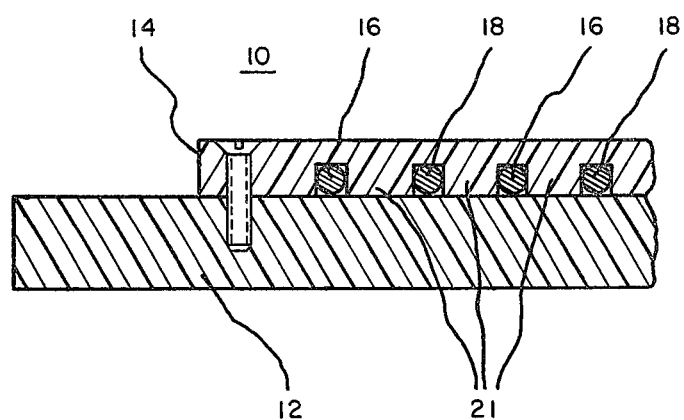
FIG. 2 is a cross-sectional view of a portion of the detector taken on line 2—2 of FIG. 1.

Detector head 10 may be constructed with a base 12 made of any non-conducting material, such as wood or plastic. An opening 19 is provided through which the drops to be measured will pass. Grounded wires 16 and positive wires 18 are held on base 12 by a spacing frame 14. The sensing wires cross opening 19 in a parallel, spaced-apart relationship with one another and they are maintained in that relationship by the configuration of spacing frame 14. As shown in FIG. 2, spacing frame 14 has a comb-like shape, having a plurality of short teeth 21 which are in direct contact with base 12. Wires 16 and 18 pass through the gaps between teeth 21 and are thereby held in a precisely determined relationship with one another, dependent upon the dimensions of teeth 21 and the gaps between them. Spacing frame 14 may be constructed of any suitable non-conducting materials such as plastic.

In constructing laboratory models of the invention, I have found it convenient to use a center-to-center spacing of $5 \times 10^{-4}$ m. Two different wire sets have been used, one measuring $7.62 \times 10^{-5}$ m. in diameter made of copper, and the other measuring $3.3 \times 10^{-5}$ m. in diameter made of stress relieved nickel. It will, therefore, be appreciated that drops as small as about $4 \times 10^{-4}$ m. in diameter can be measured with a detector head of the dimensions just indicated. Obviously, these dimensions can be changed as may be appropriate to an anticipated range of drop sizes one might wish to measure.

Any suitable voltage source may be used to maintain the potential difference between wires 16 and 18. For purposes of this invention, all that is required is that each odd numbered wire be maintained at a potential difference with respect to its neighboring even numbered wire.

The sensing wires 16 and 18 are individually connected to circuitry which is suitable for generating and storing an indication in response to a change in the potential of each wire. Such circuitry would desirably include means to amplify a change in the potential of its associated wire and this is generally indicated in FIG. 1 as amplification circuitry 20. It should be understood, however, that each wire should have its own individual amplification means associated with it. In my laboratory model, I have obtained satisfactory results with a solid state amplifier of the type numbered LM741. The output signal of each amplifier is fed into circuit components 22 intended to change its character from analog to digital form. These components might include, first, a voltage comparator into which the output of the amplifier is fed and a monostable multivibrator which is connected to the output of the comparator. Thus, a change of sufficient magnitude in the potential of a wire 16 or 18 will result in a digital pulse being produced by its associated multivibrator. Solid state devices LM311 and 74123 served satisfactorily as the voltage comparator and multivibrator, respectively, in the laboratory model. The digital outputs of the analog to digital conversion circuitry 22 are fed into an ORing circuit 26 and a data storage register 24. The output from ORing circuit 26 will produce a suitable enabling pulse to be fed into data storage register 24 whenever an input pulse appears on any of its input leads. A data storage register of type number 7475 proved to be suitable in my model. The stored data consists of a logic 1 state for each sensing wire whose potential has changed and a logic 0 state for the others. A suitable readout circuit 28 may be used to provide an indication as to the number and location of wires at the logic 1 state. This indication may take the form of a serial readout to a scaler which would count and display the number of wires contacted and/or a parallel readout to a set of LED's for visual inspection and/or readout one byte at a time to a microprocessor such as an Intel 8085 which would have the capability of counting logic 1 bit and testing for contiguity and edge wires. Associated devices can also be used to permanently record the reception of data against elapsed time.

The frequency with which liquid drops can be expected to impinge upon sensing wires 16 and 18, as well as the size of the drops involved, are, of course, parameters which will have a bearing on the configuration of the system just described. First, the size and spacing of wires 16 and 18 can be conveniently chosen to accommodate the range of drop sizes to be measured. Also requirements for reaction and recycling time of the circuitry might vary from one application to another. The laboratory model described above was used to measure drops ranging in size up to about 6 millimeters in diameter. Assuming these drops to be falling under the influence of gravity at a terminal velocity, the maximum time it takes for a drop of that size to fall a distance of 1 radius is less than 0.5 ms.

Changes and modifications in the specifically described embodiment of this invention can be carried out without departing from the scope of the invention which is intended to be limited only by the scope of the appended claims. For example, it might be advantageous for certain applications to utilize the pulses generated by this invention in real time rather than storing them. This could be accomplished with circuit components readily available in the market place.

What is claimed is:

1. A disdrometer for measuring the size of moving electrically conductive liquid drops comprising:
   a plurality of sensing wires of preselected thickness arranged in a premeasured, equally spaced-apart, parallel relationship with one another in a plane transverse to the path of the moving drops, each wire being maintained at an electric potential difference with respect to its adjacent wires; and
   circuit means for counting the number of adjacent wires whose potential momentarily changes when electrically connected to one another by a passing drop, thereby the numbers counted by said circuit means is used to mathematically determine, within predetermined limits, the size range of the drop connecting the wires.

2. The invention of claim 1 wherein the sensing wires are arranged in a detecting head comprised of a mounting base, a spacing frame to hold the wires and means for anchoring the frame on the base.

3. The invention of claim 1 or 2 wherein the circuit means includes:
   means connected to each wire for sensing a change in potential therein and providing an output signal in response to such change; and
   means connected to each sensing means for receiving the output signal and forming and storing an indication thereof as a data bit correlated to that wire.

4. The invention of claim 3 wherein each sensing means is comprised of:
   means connected to each wire for amplifying a change in potential therein; and
   means connected to the output of the amplifier means and responsive to the amplified change in potential for producing a pulse.

5. The invention of claim 4 wherein the receiving and storing means is comprised of:
   a storage register having a storage location correlated to each wire for storing an indication when a pulse is received from a pulse producing means; and
   logic circuit means connected between the pulse producing means and the storage register for enabling the storage register whenever pulses are received from any pulse producing means.

6. The invention of claim 5 in further combination with circuit means for providing a readout of the data bits contained in the storage register.

7. A method for determining the size of moving electrically conductive liquid drops comprising the steps of:
   positioning a plurality of sensing wires in the path of movement of the drops, said wires being of preselected thickness and arranged in a premeasured, equally spaced-apart, parallel relationship with one another;

maintaining each wire at a potential difference with respect to its adjacent wires and counting the number of adjacent wires whose potential momemtarily changes when electrically connected to one another by a passing drop, thereby the counted number is used to mathematically determine the size of the drop connecting the wires.

8. The method of claim 7 wherein said positioning step includes the following steps:

arranging the wires in a detecting head comprised of a mounting base and a spacing frame to hold the wires; and anchoring the frame on the base.

9. The method of claim 7 or 8 wherein said counting step includes the steps of:

amplifying a change in potential, occurring in an individual wire;

producing a pulse from the amplified change in potential of a wire; and counting the number of adjacent wires for which a pulse is produced.

10. The method of claim 9 wherein the counting step includes the intermediate steps of storing an indication of the pulses produced in locations correlated to each wire and subsequently providing a readout of the stored indications.

* * * * *